United States Patent [19]
Kao et al.

[11] Patent Number: 6,069,109
[45] Date of Patent: May 30, 2000

[54] PROCESS FOR THE PRODUCTION OF HALF-SANDWICH TRANSITION METAL BASED CATALYST PRECURSORS

[75] Inventors: Sun-Chueh Kao; Frederick John Karol, both of Belle Mead, N.J.

[73] Assignee: Union Carbide Chemicals & Plastics Technology Corporation, Danbury, Conn.

[21] Appl. No.: 09/108,824

[22] Filed: Jul. 1, 1998

[51] Int. Cl.$^7$ .............................. B01J 31/00; C07F 7/00; C07F 7/28

[52] U.S. Cl. .................... 502/152; 502/155; 502/170; 556/11; 556/14; 556/52; 556/55

[58] Field of Search ................... 556/11, 14, 52, 556/55; 502/152, 155, 170

[56] References Cited

U.S. PATENT DOCUMENTS 5,527,752   6/1996   Reichle et al. ........................ 502/117

FOREIGN PATENT DOCUMENTS

0798313A1   10/1997   European Pat. Off. .

OTHER PUBLICATIONS

A.N. Chernega et al., J.C.S. Chem. Commun., 1993, pp. 1415–1417, no month available.

A.K. Hughes et al., Organometallics, May 1993, vol. 12, No. 5, pp. 1936–1945.

Wailes, P.C. et al, "Hydrido Complexes of Zirconium II. Reactions of Dicyclopentadienylzirconium Dihydride With Carboxylic Acids", J. Organometal. Chem., 24 (1970) 413–417, no month.

Brainina, E.M. et al, "Some Properties of Tetracyclopentadienylzirconium", Institute of Heteroorganic Compounds, Academy of Sciences, USSR Translated from Izvestiya Akademii Nauk SSSR, Seriya Khimicheskaya, No. 10, pp. 1877–1879, Oct., 1965. Original Article Submitted Feb. 2, 1965.

Brainina, E.M. et al, "Cyclopentadienyl Zirconium Compounds Containing Acyloxy Groups", Institute of Heteroorganic Compounds, Academy of Sciences, USSR Translated from Izvestiya Akademii Nauk SSSR, Otdelenie Khimicheskikh Nauk, No. 5, pp. 835–838, May, 1963. Original Article Submitted Jun. 20, 1962.

Article; Brintzinger et al.; "Zirconocene Dipicolinate and Related Dicarboxylate Complexes: Coordination Geometries and Reactivities"; Journal of Organometallic Chemistry 456 (1993) 195–204.

Article; Kohn et al.; "Acylation Reactions Mediated by Tantalum Carboxylates"; J. Am. Chem. Soc. 1992, 114, 6649–6652.

*Primary Examiner*—Mark L. Bell
*Assistant Examiner*—J. Pasterczyk
*Attorney, Agent, or Firm*—P. W. Leuzzi

[57] ABSTRACT

A process for the production of a catalyst precursor comprising reacting (a) a metallocene dihalide; (b) a compound of the formula:

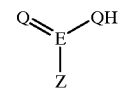

wherein each Q is the same or different and is independently selected from the group consisting of O, NR, $CR_2$, and S; E is either C or S; Z is selected from the group consisting of —OR, —$NR_2$, —$CR_3$, —SR, —$SiR_3$, —$PR_2$, —H, and a substituted or unsubstituted aryl group; and each R is independently a group containing carbon, silicon, nitrogen, oxygen, and/or phosphorus; and (c) a trialkylamine.

8 Claims, No Drawings

PROCESS FOR THE PRODUCTION OF HALF-SANDWICH TRANSITION METAL BASED CATALYST PRECURSORS

FIELD

The present invention relates to an improved process for producing half-sandwich transition metal based catalysts. These catalysts are generally useful in the production of polyolefins, such as polyethylene, polypropylene and their copolymers with other alpha-olefins. More specifically, this invention relates to a process for producing complexes of transition metals, substituted or unsubstituted π-bonded ligands and heteroallyl moieties.

BACKGROUND

Numerous catalysts have been developed which provide polyolefins with certain advantageous properties. One class of these catalysts are now commonly referred to as metallocenes, organometallic coordination complexes containing one or more π-bonded moieties in association with a metal atom from Groups IIIB to VIII or the Lanthanide series of the Periodic Table of Elements. These catalysts are reportedly highly useful in the preparation of polyolefins because they produce homogeneous polymers at excellent polymerization rates, allowing one to closely tailor the final properties of the polymer as desired.

In U.S. Pat. No. 5,527,752 a novel catalyst precursor was disclosed for use in the manufacture of polyolefins. However, the manufacture of this catalyst on a commercial scale is frustrated by the required employment of cryogenic cooling during the protonation step. This is a complex and costly step to undertake and it makes this class of metallocenes very expensive to manufacture. Accordingly, there existed a need for a simpler procedure for its manufacture.

SUMMARY OF THE INVENTION

The invention provides an improved process for producing half-sandwich transition metal based catalyst of either Formula I or Formula II as set forth below.

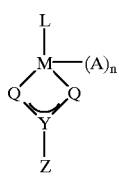

Formula I wherein:
M is a metal atom from Groups IIIB to VIII or the Lanthanide series of the Periodic Table of Elements, preferably Ti, Zr or Hf;
L is a substituted or unsubstituted, π-bonded ligand coordinated to M, preferably a cyclopentadienyl-type ligand;
Q can be the same or different and is independently selected from the group consisting of —O—, —NR—, —CR$_2$— and —S—;
Y is either C or S;
Z is selected from the group consisting of —OR, —NR$_2$, —CR$_3$, —SR, —SiR$_3$, —PR$_2$, —H, and substituted or unsubstituted aryl group with the proviso that when Q is —NR— then Z is selected from the group consisting of —OR, —NR$_2$, —SR, —SiR$_3$, —PR$_2$ and —H;

n is 1 or 2;
A is a univalent anionic group when n is 2 or A is a divalent anionic group when n is 1; when n is 2, A can be the group formed by QYQZ depicted in formula I above; and
R can be the same or different and is independently a group containing carbon, silicon, nitrogen, oxygen, and/or phosphorus where one or more R groups may be attached to the L substituent, preferably R is a hydrocarbon group containing from 1 to 20 carbon atoms, most preferably an alkyl, cycloalkyl or an aryl group.

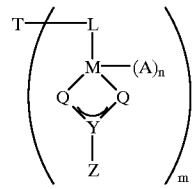

Formula II wherein:
M is a metal atom from Groups IIIB to VIII or the Lanthanide series of the Periodic Table of Elements, preferably Ti, Zr or Hf;
L is a substituted or unsubstituted, π-bonded ligand coordinated to M, preferably a cyclopentadienyl-type ligand;
Q can be the same or different and is independently selected from the group consisting of —O—, —NR—, —CR$_2$—and —S—
Y is either C or S;
Z is selected from the group consisting of —OR, —NR$_2$, —CR$_3$, —SR,—SiR$_3$, —PR$_2$, —H, and substituted or unsubstituted aryl group with the proviso that when Q is —NR— then Z is selected from the group consisting of —OR, —NR$_2$, —SR, —SiR$_3$, —PR$_2$ and —H;
n is 1 or 2;
A is a univalent anionic group when n is 2 or A is a divalent anionic group when n is 1; when n is 2, A can be the group formed by QYQZ depicted in formula II above;
R can be the same or different and is independently a group containing carbon, silicon, nitrogen, oxygen, and/or phosphorus where one or more R groups may be attached to the L substituent, preferably R is a hydrocarbon group containing from 1 to 20 carbon atoms, most preferably an alkyl, cycloalkyl or an aryl group;
T is a bridging group selected from the group consisting of an alkylene or arylene group containing from 1 to 10 carbon atoms optionally substituted with carbon or heteroatoms, germanium silicon and alkyl phosphine; and
m is 1 to 7, preferably 2 to 6, most preferably 2 or 3.

The process employs the use of a metallocene dihalide as the starting material for the transition metal and trialkylamine as the halide removing agent. Using these two materials, and an organic acid, a simple, mild, low cost manufacturing process for compounds of Formula I and II is provided. Previously, these compounds were produced by reacting a metallocene dichloride and an organic acid without trialkylamine. When such an approach was employed, the organic acid had to be used in large excess and the preparation had to be conducted under vigorous conditions. Since organic acids are corrosive and irritant, the use of a large excess of these materials under such vigorous conditions raised safety concerns for their employment in a commercial scale operation. Furthermore, since the organic acids were used both as a reactant and as the reaction medium, this method was not suitable for organic acids that were solid under the reaction condition. The present invention has surprisingly overcome these deficiencies.

DETAILED DESCRIPTION OF THE INVENTION

According to the present invention, the half-sandwich transition metal based catalysts may be made by reacting in a hydrocarbon medium at from about 20° C. to 60° C. for approximately one to ten hours under an inert atmosphere, preferably nitrogen, (a) 1 equivalent of a metallocene dihalide of Formula III with (b) 3 equivalents of an organic acid of Formula IV and (c) 3 equivalents of a trialkylamine and thereafter recovering the product. The half-sandwich transition metal based catalysts so prepared generally has a purity which exceeds 95% and thus depending on its use may require no further purification.

The metallocene dihalide is of the formula:

$(L)(L')MX_2$  Formula III wherein M is a metal atom from Groups IIIB to VIII or the Lanthanide series of the Periodic Table of Elements, preferably Ti, Zr or Hf; X is a halogen atom; L and L' are the same or different, may be bridged to each other or unbridged and are independently a substituted or unsubstituted, π-bonded ligand coordinated to M, such as cyclopentadienyl, indenyl, tetrahydroindenyl, or fluorenyl groups. Generally, when substituted the ligand will be substituted with one or more hydrocarbon groups containing from 1 to 20 carbon atoms, most preferably an alkyl, cycloalkyl or an aryl group.

The organic acid is of the forumla:

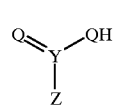

Formula IV wherein Q can be the same or different and is independently selected from the group consisting of —O, —NR, —CR$_2$ and —S; Y is either C or S; Z is selected from the group consisting of —OR, —NR$_2$, —CR$_3$, —SR, SiR$_3$, —PR$_2$, —H, substituted or unsubstituted aryl groups; and R can be same or different and is independently a group containing carbon, silicon, nitrogen, oxygen, and/or phosphorus, preferably R is a hydrocarbon group containing from 1 to 20 carbon atoms, most preferably an alkyl, cycloalkyl or an aryl group;

and the trialkylamine is of the formula NR'$_3$ wherein R' is a hydrocarbon group containing from 1 to 20 carbon atoms, most preferably an alkyl, cycloalkyl or an aryl group.

The reactants may be sourced from any of a variety of well known suppliers, for instance the metallocene dihalide can be obtained from Witco Corporation and the organic acid and trialkylanine can be obtained from Aldrich Chemical Company.

These half-sandwich transition metal based catalysts are used with an activator, such as aluminoxane, to form the active catalyst.

Examples of the half-sandwich transition metal based catalysts include, but are not limited to, indenyl zirconium tris(pivalate), indenyl zirconium tris(p-toluate), indenyl zirconium tris(benzoate), (1-methylindenyl) zirconium tris (pivalate), (2-meth-ylindenyl) zirconium tris (diethylcarbamate), (methylcyclopentadienyl) zirconium tris(pivalate), (cyclopentadienyl) zirconium tris(pivalate), (pentamethylcyclopentadienyl) zirconium tris(benzoate), n-butylcyclopentadienylzirconium trispivalate, (n-butylcyclopenta-dienyl)tris(benzoate), (tetrahydroindenyl)zirconium tris(pivalate), (tetrahydroindenyl)zirconium tris(benzoate), (tetrahydroindenyl)zirconium tris(pentenate), (1,3-dimethylcyclopentadienyl)zirconium tris(pivalate), (1,3-methylethyl-cyclopentadienyl)zirconium tris(pivalate), (tetramethylcyclopentadienyl)zirconium tris(pivalate), (pentamethylcyclopentadienyl)zirconium tris(pivalate), (cyclopentylcyclopentadienyl)zirconium tris(benzoate), (benzylcyclopentadienyl)zirconium tris(benzoate), (n-butylcyclopentadienyl)hafnium tris(pivalate), (n-butylcyclopentadienyl)titanium tris(pivalate).

As noted above, these catalyst precursors are used in conjunction with activating cocatalysts to form catalyst compositions for the production of polyolefins. Preferably, the activating cocatalysts are one of the following: (a) branched or cyclic oligomeric poly(hydrocarbylaluminum oxide) that contain repeating units of the general formula —(Al(R)O)—, where R is an alkyl radical containing from 1 to about 12 carbon atoms, or an aryl radical such as a substituted or unsubstituted phenyl or naphthyl group or (b) non-coordinating anions, such as tri(pentafluorophenyl) borate, triethyl tetra(pentafluorophenyl) borate and the like. For a more detailed discussion of non-coordinating anions see U.S. Pat. No. 5, 599,761.

Preferably, the activating cocatalyst is a branched or cyclic oligomeric poly(hydrocarbylaluminum oxide). More preferably, the activating cocatalyst is an aluminoxane such as methylaluminoxane (MAO) or modified methylaluminoxane (MMAO).

The amount of catalyst usefully employed in the catalyst composition may vary over a wide range. It is generally preferred to use the catalyst compositions at concentrations sufficient to provide at least about 0.000001, preferably about 0.00001 percent, by weight, of transition metal based on the weight of the monomers. The upper limit of the percentages is determined by a combination of catalyst activity and process economics. When the activating cocatalyst is a branched or cyclic oligomeric poly (hydrocarbylaluminum oxide), the mole ratio of aluminum atoms contained in the poly(hydrocarbylaluminum oxide) to transition metal atoms contained in the catalyst of the present invention is generally in the range of about 2:1 to about 100,000:1, preferably in the range of about 10:1 to about 10,000:1, and most preferably in the range of about 50:1 to about 2,000:1.

The catalyst composition may optionally contain one or more other polyolefin catalysts. These catalysts include, for example, any Ziegler-Natta catalysts containing a metal from groups IV(B), V(B), or VI(B) of the Periodic Table. Suitable activators for Ziegler-Natta catalysts are well known in the art and may also be included in the catalyst composition.

The catalyst composition may be supported or unsupported. In the case of a supported catalyst composition, the catalyst and the activating cocatalyst may be impregnated in or deposited on the surface of a substrate such as silicon dioxide, aluminum oxide, magnesium dichloride, polystyrene, polyethylene, polypropylene, or polycarbonate, such that the catalyst composition is between 0.01 and 90 percent by weight of the total weight of the catalyst composition and the support.

The support may first be impregnated with a hydrocarbon solution of the co-catalyst, dried of solvent followed by reimpregnation with the metal catalyst solution followed by solvent removal. Alternatively, the base support may be impregnated with the reaction product of the metal catalyst precursor and the co-catalyst followed by removal of the solvent. In either case, a hydrocarbon slurry of the supported, activated catalyst or a hydrocarbon-free powder results and these are used, usually without added activator as olefin polymerization catalysts. Frequently, an impurity scavenger is added to the reaction prior to or along with the catalyst-cocatalyst slurry/powder in order to maximize its activity.

Alternatively, the support can first be heated to drive off hydroxylic impurities notably water followed by reaction of the remaining hydroxyl groups with proton scavengers such as hydrocarbaryl aluminum compounds (TMA, TEA, TIBAL, TNHAL, MAO, MMAO, etc.). Also, the heating may be omitted and the support reacted directly with the hydrocarbonyl aluminum compounds.

Polymerization may be conducted in the gas phase in a stirred or fluidized bed reactor, or in a high pressure, solution or slurry phase reactor using equipment and procedures well known in the art. Generally, the polymerization temperature ranges from about 0° C. to about 200° C. at atmospheric, subatmospheric or superatmospheric pressures. A slurry or solution polymerization process can utilize subatmospheric and superatmospheric pressures and temperatures in the range of about 40° C. to about 110° C. In the present invention, is preferred to utilize a gas phase polymerization process with superatmosheric pressures in the range of 1 to 1000 psi, preferably 50 to 400 psi and most preferably 100 to 300 psi, at temeratures in the range of 30 to 130° C., preferably 65 to 110° C. Ethylene, higher alpha-olefin(s), and optionally other monomers are contacted with an effective amount of catalyst composition at a temperature and a pressure sufficient to initiate polymerization. The process may be carried out in a single reactor or in two or more reactors in series. The process is conducted substantially in the absence of catalyst poisons because such materials have been found to affect the polymerization adversely. Organometallic compounds may be employed as scavenging agents for poisons to increase the catalyst activity. Examples of these compounds are metal alkyls, preferably aluminum alkyls, most preferably triisobutylaluminum.

Conventional adjuvants may be included in the process, provided they do not interfere with the operation of the catalyst composition in forming the desired polyolefin. Hydrogen can be used as a chain transfer agent in the process, in amounts up to about 10 moles of hydrogen per mole of total monomer feed.

Also, as desired for temperature control of the system, any gas inert to the catalyst composition and reactants can also be present in the gas stream.

Generally, the alpha-olefin monomers have from 2 to 12 carbon atoms and typically include, but not limited to, ethylene, propylene, 1-butene, 1-pentene, 4-methyl-1-pentene, 1-hexene, styrene, and the like. Preferred dienes which may optionally be polymerized with the alpha-olefins are those which are non-conjugated. These non-conjugated diene monomers may be straight chain, branched chain or cyclic hydrocarbon dienes having from about 5 to about 15 carbon atoms. Dienes which are especially preferred include 1,5-hexadiene, 5-vinyl-2-norbornene, 1,7-octadiene and the like.

Preferred aromatic compounds having vinyl unsaturation may be optionally polymerized with the alpha-olefins include styrene and substituted styrenes.

Polyolefins produced according to the invention can be polymers of one or more olefins. The polyolefins may also be derived from diolefins such as divinylbenzene, isoprene, linear terminal diolefins such as 1,7-octadiene, or olefins having one or more strained double bonds such as bicyclo (2.2.1) hepta-2,5-diene, 5-ethylidine-2-norbornene, 5-vinyl-2-norborene (endo and exo forms or mixtures thereof) and normal mono-olefins.

Catalyst additives may be introduced into the reaction zone as part of the catalyst system to modify reaction rates, such as Lewis bases. The Lewis bases which are applicable for use in the present invention and which are capable of reducing the activity of the olefin polymerization reaction as desired, even to the point of substantially complete termination, which is fully reversible, include ethers, alcohols, ketones, aldehydes, carboxylic acids, esters, carbonates, phosphines, phosphine oxides, phosphates, phosphites, amines, amides, nitrites, alkoxy silanes, aluminum alkoxides, water, oxygen, nitric oxides, and the like.

The Lewis base may be added to the polymerization reaction by a variety of methods, depending upon the polymerization process being used and the form of the Lewis base. It may be added in the neat form or it may be added as a dilute solution. Depending upon the solubility of the Lewis base, appropriate diluents may include the monomer or a hydrocarbon such as toluene or isopentane.

The amounts of Lewis base that is utilized to reduce the activity of the olefin polymerization reaction using a heteroallyl/aluminoxane catalyst system is strongly dependent upon a number of factors. Those factors include the specific Lewis base being used, the specific catalyst precursor compound that is present, the specific aluminoxane compound that is present, the reaction temperature, the molar ratio of aluminoxane to catalyst precursor, the specific olefin(s) that is(are) present, and the concentration of the olefin used in the polymerization reaction. Generally, if a multifunctional Lewis base is utilized to reduce the activity of the olefin polymerization, the extent of the reduction in polymerization activity will be greater than that observed with an equivalent amount of a monofunctional Lewis base. The amounts of Lewis base required to reduce the activity of a polymerization reaction will be less if a low aluminoxane catalyst precursor ratio is utilized.

The gas phase olefin polymerization reaction systems in which the present invention is useful comprise a reactor vessel to which olefin monomer and catalyst components can be added and which contain a bed of forming polyolefin particles. The present invention is not limited to any specific type of gas phase reaction system. In very general terms, a conventional fluidized bed process for producing resins is conducted by passing a gaseous stream containing one or more monomers continuously through a fluidized bed reactor under reaction conditions and in the presence of catalyst at a velocity sufficient to maintain the bed of solid particles in a suspended condition. The gaseous stream containing unreacted gaseous monomer is withdrawn from the reactor continuously, compressed, cooled and recycled into the reactor. Product is withdrawn from the reactor and make-up monomer is added to the recycle stream.

One of the liquid phase olefin polymerization reaction systems in which the present invention is useful is described in U.S. Pat. No. 3,324,095. The liquid phase olefin polymerization reaction systems generally comprise a reactor vessel to which olefin monomer and catalyst components can be added and which contains liquid reaction medium for dissolving or suspending the polyolefin. The liquid medium may consist of the bulk liquid monomer or an inert liquid hydrocarbon which is nonreactive under the polymerization conditions employed. While the hydrocarbon selected need not function as solvent for the catalyst or the polymers obtained by the process, it usually serves as solvent for the monomers employed in the polymerization. Among the inert hydrocarbon liquids suitable for this purpose may be mentioned isopentane, hexane, cyclohexane, heptane, benzene, toluene, and the like. The present invention is not limited to any specific type of solution, slurry, or bulk liquid monomer reaction system. In very general terms, a conventional liquid phase olefin process for producing resins is conducted by continuously adding one or more monomers to a reactor under reaction conditions in the presence of catalyst at a concentration sufficient to maintain the reaction medium in a fluid state. The reactive contact between the olefin monomer and the catalyst should be maintained by constant stirring or agitation of the reaction mixture. The reaction medium containing the polyolefin product and unreacted gaseous monomer is withdrawn from the reactor continuously. The polyolefin product is separated, then the unreacted monomer and liquid reaction medium are recycled into the reactor.

Whereas the exact scope of the instant invention is set forth in the appended claims, the following specific examples illustrate certain aspects of the present invention and, more particularly, point out methods of evaluating the same. However, the examples are set forth for illustration only and are not to be construed as limitations on the present invention except as set forth in the appended claims. All parts and percentages are by weight unless otherwise specified.

EXAMPLES

Example 1

Synthesis of Tetrahydroindenylzirconium trispivalate

To a solution of bis(tetrahydroindenyl)zirconium dichloride (1.182 g, 2.950 mmol) and pivalic acid (0.900 g, 8.810 mmol) in toluene (45 ml) at 25° C. was added triethylamine (0.871 g, 8.610 mmol) with stirring. A white precipaitate formed immediately which was removed by filtration. The title compound was isolated as a pale-yellow powder in 75% yield by evaporating the solvent under vacuum. The title compound such prepared exhibit purity above 98% based on NMR results. $^1$H NMR (toluene-$d_8$)δ 6.24 (t, J=3.1 Hz, 1H), 5.85 (d, J-3.1 Hz, 2H), 2.72 (m, 2H), 2.48 (m, 2H), 1.91 (m, 2H), 1.49 (m, 2H), 1.14 (s, 27H0. $^{13}$C NMR (toluene-$d_8$) δ 200 and 197 ($CO_2$), 114.4 and 114.1 (Cp), 39.2 ($CMe_3$), 26.48 ($CH_3$), 23.8 and 22.7 ($CH_2$).

Example 2

Scale-up Synthesis of Tetrahydroindenylzirconium trispivalate

A toluene solution of bis (tetrahydroindenyl)zirconium dicholride (THInZ) and pivalic acid was prepared by dissolving 400 g (0.995 mole) of THInZ and 310 g (3.030 mole) of pivalic acid in 12 liter of dry, degassed toluene. This solution was stirred at 50° C. while 304 g (3.030 mole) of neat, degassed triethylamine was slowly added over 30 minutes. A white precipitate formed immediately and the resulting slurry was stirred at 40° C. for two hours, hexane (3 liters) was added and the mixture was stirred for one more hour. The solids were removed by filtering through a 1 micron bag filter by pumping the solution from the still through the filter and back to the still. The resulting solution was concentrated in the still under reduced pressure with a stream of nitrogen at @ 65° C. to yield about 800 ml of yellow solution, containing about 50 weight percent product. This solution was filtered once more, to remove a small amount of fines, the remaining toluene was evaporated, all in the glove box. Both proton and carbon NMRs of the resulting pale-yellow powder (477 g) were examined and a purity of more than 98% was found. The yield for this preparation was 93%.

Example 3

Synthesis of (n-butylcyclopentadienyl)zirconium trispivalate

To a solution of bis(n-butylcyclopentadienyl)zirconium dichloride (1.001 g, 2.477 mmol) and pivalic acid (0.760 g, 7.451 mmol) in toluene (25 ml) at 25° C. was added triethylamine (0.871 g, 8.610 mmol) with stirring. A white precipitate formed immediately which was removed by filtration. The title compound was isolated as a light orange oil in 78% yield by evaporating the solvent under vacuum. The title compound such prepared exhibit purity above 95% based on MNR results. $^1$H NMR (toluene-$d_8$) δ 6.22 (m,2H), 5.97 (m,2H), 2.61 (t,J=7.7 Hz, 2H), 1.51 (m, 2H), 1.29 (m, 2H), 1.11 (s, 27H), 0.87 (t, J=7.2 Hz 3H).

Example 4

Synthesis of (n-butylcyclopentadienyl)zirconium trisbenzoate

To a solution of bis (n-butylcyclopentadienyl)zirconium dichloride (1.001 g, 2.477 mmol) and benzoic acid (0.900 g, 7.371 mmol) in toluene (40 ml) at 25° C. was added triethylamine (0.871 g, 8.610 mmol) with stirring. A white precipitate formed immediately which was removed by filtration. The title compound was isolated as a dark yellow oil in 84% yield by evaporating the solvent under vacuum. The title compound such prepared exhibit purity above 95% based on NMR results. $^1$H NMR (toluene-$d_8$) δ 8.08 (s,6H), 7.01 (m,9H), 6.47 (m,2H), 6.22 (m, 2H), 2.80(t,J=7.6 Hz, 2H), 1.54 (m, 2H), 1.26 (m, 2H), 0.84 (t, J=7.2 Hz 3H).

Example 5

Synthesis of (n-butylcyclopentadienyl)hafnium Trispivalate

To a solution of bis(n-butylcyclopentadienyl)hafnium dichloride (0.500 g, 1.012 mmol) and pivalic acid (0.330 g, 3.230 mmol) in toluene (30 ml) at 50° C. was added triethylamine (0.363 g, 3.240 mmol) with stirring. A white precipitate formed immediately which was removed by filtration. The title compound was isolated as a dark yellow oil in 66% yield by evaporating the solvent under vacuum. The title compound such prepared exhibit purity above 95% based on NMR results. $^1$H NMR (toluene-$d_8$) δ 6.15 (m, 2H), 5.90 (m,2H), 2.67 (t,J=7.6 Hz, 2H), 1.54 (m, 2H), 1.31 (m, 2H), 1.13 (s, 27H), 0.88 (t, J=7.2 Hz, 3H).

Example 6

Synthesis of pentamethylcyclopentadienylzirconium Trispivalate

To a solution of (pentamethylcyclopentadienyl)(n-propylcyclopentadienyl)-zirconium dichloride (1.050 g, 2.598 mmol ) and pivalic acid (0.933 g, 9.147 mmol ) in toluene (35 ml) at 40 C. was added triethylamine (0.871 g, 8.609 mmol ) with stirring. A white precipitate formed immediately which was removed by filtration. The title compound was isolated as a pale yellow powder in 73% yield by evaporating the solvent under vacuum with mild heating. The title compound such prepared exhibited purity about 97% based on NMR results. $^1$H NMR (toluene$_8$) δ 1.92 (s, 15H), 1.14 (s, 27H).

We claim:

1. A process for the production of a half-sandwich transition metal catalyst precursor comprising:

(I) reacting, in a hydrocarbon medium at a temperature from about 20 to about 60 degrees ° C. for approximately one to ten hours under an inert atmosphere, (a) 1 equivalent of a metallocene dihalide of the formula (L)(L')MX$_2$ wherein M is a metal atom from Groups 4 to 6 of the Periodic Table; X is a halogen atom; and L and L' are the same or different; are bridged to each other or unbridged; and are each independently a substituted or unsubstituted π-bonded ligand coordinated to M; (b) 3 equivalents of a compound of the formula:

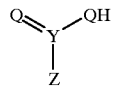

wherein each Q is the same or different and is independently selected from the group consisting of O, NR, CR$_2$, and S; Y is either C or S; Z is selected from the group consisting of —OR, —NR$_2$, —CR$_3$, —SR, —SiR$_3$, —PR$_2$, —H, and a substituted or unsubstituted aryl group; and each R is independently a group containing carbon, silicon, nitrogen, oxygen, and/or phosphorus, and (c) 3 equivalents of a trialkylamine of the formula NR'$_3$ wherein R' is a hydrocarbon group containing from 1 to 20 carbon atoms; and (II) recovering the product.

2. The process of claim 1 wherein M is Ti, Zr, or Hf.

3. The process of claim 1 wherein L and L' are selected from the group consisting of substituted or unsubstituted cyclopentadienyl, indenyl, tetrahydroindenyl, and fluorenyl groups.

4. The process of claim 3 wherein L and L' are substituted with one or more alkyl, cycloalkyl or aryl groups containing from 1 to 20 carbon atoms.

5. The process of claim 1 wherein R is a hydrocarbon group containing []from 1 to 20 carbon atoms.

6. The process of claim 5 wherein the hydrocarbon group is an alkyl, cycloalkyl, or an aryl group.

7. The process of claim 1 wherein R' is an alkyl, cycloalkyl, or an aryl group.

8. A process for the production of a half-sandwich transition metal catalyst precursor comprising (I) reacting, in a hydrocarbon medium at a temperature from about 30 to about 50 degrees ° C. for approximately one to three hours under an inert atmosphere, (a) 1 equivalent of a metallocene dihalide of the formula (L)(L')MX$_2$ wherein M is Ti, Zr, or Hf; X is a halogen atom; and L and L' are the same or different; are bridged to each other or unbridged; and are each independently a substituted or unsubstituted cyclopentadienyl, indenyl, tetrahydroindenyl, or fluorenyl group coordinated to M; (b) 3 equivalents of a compound of the formula:

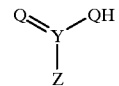

wherein each Q is the same or different and is independently selected from the group consisting of O, NR, CR$_2$, and S; Y is either C or S; Z is selected from the group consisting of —OR, —NR$_2$, —CR$_3$, —SR, SiR$_3$, —PR$_2$, —H, and a substituted or unsubstituted aryl group; and each R is independently an alkyl, cycloalkyl, or an aryl group containing 1 to 20 carbon atoms, and (c) 3 equivalents of a trialkylamine of the formula NR'$_3$ wherein R' is an alkyl, cycloalkyl, or an aryl group containing 1 to 20 carbon atoms; and (II) recovering the product.

* * * * *